United States Patent [19]

Tanabe et al.

[11] 4,109,000
[45] Aug. 22, 1978

[54] 5-BENZYLPICOLINIC ACID DERIVATIVES

[75] Inventors: Osamu Tanabe; Akiro Obayashi, both of Uji; Teruya Nakamura, Muko; Osamu Suzuka; Masao Murayama, both of Kyoto; Hiromu Murai, Otsu, all of Japan

[73] Assignees: Nippon Shinyaku Co., Ltd.; Takara Shuzo Co., Ltd., both of Japan

[21] Appl. No.: 696,549

[22] Filed: Jun. 16, 1976

Related U.S. Application Data

[63] Continuation-in-part of Ser. No. 648,626, Jan. 13, 1976, abandoned, and Ser. No. 607,039, Aug. 22, 1975, Pat. No. 4,009,077, which is a continuation-in-part of Ser. No. 582,766, Jun. 2, 1975, abandoned.

[30] Foreign Application Priority Data

| Jan. 22, 1975 | [JP] | Japan | 50-9998 |
| Jan. 22, 1975 | [JP] | Japan | 50-9999 |
| Jan. 22, 1975 | [JP] | Japan | 50-10000 |
| Jan. 22, 1975 | [JP] | Japan | 50-10001 |
| Jan. 22, 1975 | [JP] | Japan | 50-10002 |
| Jan. 22, 1975 | [JP] | Japan | 50-10003 |

[51] Int. Cl.$^2$ ............... A61K 31/44; C07D 213/69

[52] U.S. Cl. ............... 424/263; 260/290 R; 260/295 AM; 260/295 PA; 260/295 R
[58] Field of Search .... 260/295 R, 295 AM, 295 PA; 424/263

[56] References Cited

U.S. PATENT DOCUMENTS 3,585,206  6/1971  Daniels ........................... 260/295

Primary Examiner—Donald G. Daus
Assistant Examiner—Lisa Jones
Attorney, Agent, or Firm—Jacobs & Jacobs

[57] ABSTRACT

5-Benzy-2-pyridine carboxylic acids, in which the benzyl group is optionally substituted by one or two like or different alkyl, halo, alkoxy, nitro, amino, acetamido, hydroxy or acetoxy groups, and the corresponding amides and esters, possess dopamine $\beta$-hydroxylase inhibitory properties and are useful as blood pressure lowering agents. The compounds, of which 5-(4-chlorobenzyl)-2-pyridine carboxylic acid, 5-(4-hydroxybenzyl)-2-pyridine carboxylic acid and 5-benzyl-2-pyridine carboxylic acid are typical examples, can be prepared by a number of chemical methods.

26 Claims, No Drawings

5-BENZYLPICOLINIC ACID DERIVATIVES

CROSS-REFERENCE

This is a continuation-in-part of Ser. Nos. 648,626 and 607,039 filed Jan. 13, 1976 and Aug. 22, 1975, respectively, Ser. No. 648,626 now being abandoned and Ser. No. 607,039, now U.S. Pat. No. 4,009,077 in turn being a continuation-in-part of Ser. No. 582,766 filed June 2, 1975, now abandoned.

DETAILED DESCRIPTION

The present invention pertains to 5-benzylpicolinic acid derivatives and to their use as hypotensive agents.

In particular the present invention pertains to compounds of the formula:

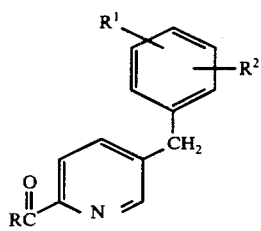

I wherein
R is hydroxy, lower alkoxy or

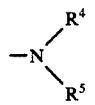

in which each of $R^4$ and $R^5$, independently of the other, is hydrogen, lower alkyl, benzyl, phenethyl or phenyl; and
each of $R^1$ and $R^2$, independently of the other, is hydrogen, lower alkyl, halo, lower alkoxy, nitro, amino, acetamido, hydroxy or acetoxy,
and the pharmaceutically acceptable salts thereof.

In a first embodiment the invention pertains to compounds wherein R is hydroxy.

In a further embodiment the invention pertains to compounds wherein R is lower alkoxy.

In a further embodiment the invention pertains to compounds wherein R if

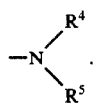

In a further embodiment the inventionn pertains to compounds wherein one of $R^1$ and $R^2$ is other than hydrogen.

In a further embodiment the invention pertains to compounds wherein $R^1$ and $R^2$ are each hydroxy or methoxy.

In a further embodiment the invention pertains to compounds wherein $R^2$ is hydrogen and $R^1$ is other than hydrogen.

In a further embodiment the invention pertains to compounds wherein $R^1$ is methyl, chloro, bromo, methoxy, ethoxy, nitro, amino, acetamido or acetoxy.

In a further embodiment the invention pertains to compounds wherein $R^1$ is in the 2- or 4-position of the depicted benzyl group.

In a further embodiment the invention pertains to compounds wherein $R^1$ is hydroxy.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

The term halo denotes the monovalent substituents fluoro, chloro, bromo and iodo.

The compounds of this invention can be prepared by various routes. Compounds wherein R is OH are prepared by oxidizing the corresponding methylpyridine (Formula II):

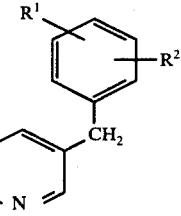

II wherein $R_1$ and $R^2$ are as defined above. Compound II is thus heated in, for example, pyridine in the presence of selenium dioxide to obtain the oxidation product of Formula I wherein R is hydroxy.

Alternatively, the compound of Formula II is oxidized with a peracid such as peracetic acid to form an N-oxide of Formula III, which is then heated in acetic anhydride to obtain an acetate of Formula IV, which is then hydrolyzed with an acid or an alkali to obtain a hydroxymethyl compound of Formula V, and which is finally oxidized with, for example, permanganic acid to obtain the compound of Formula I wherein R is hydroxy. This is as shown in the following reaction scheme:

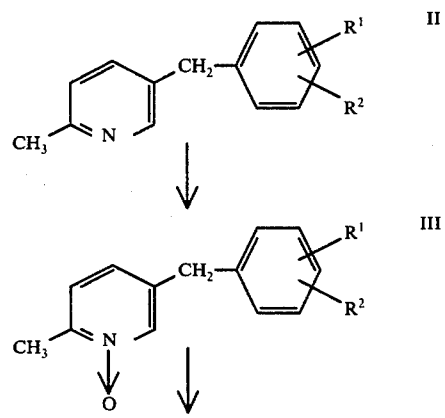

3

-continued

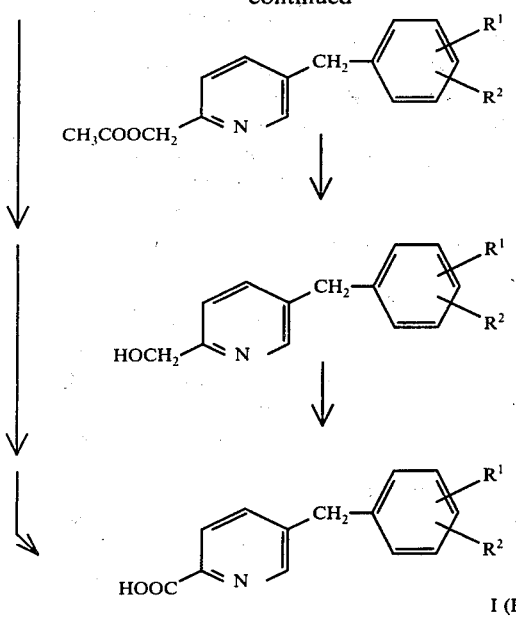

The compounds wherein $R^2$ is hydrogen and $R^1$ is nitro can also be prepared by nitration, as for example, with nitric acid or a salt thereof in sulfuric acid. This can be graphically depicted as follows:

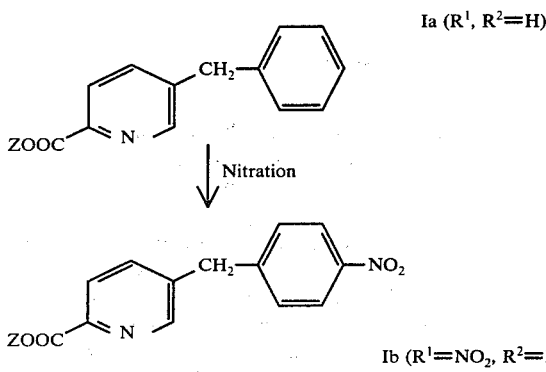

wherein Z = hydrogen or lower alkyl.

The thus nitrated compounds can be converted into the corresponding amino compounds of the formula:

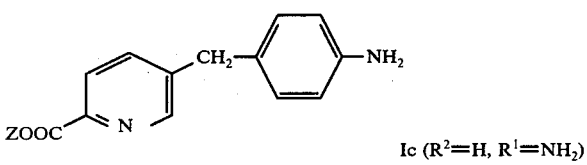

wherein Z has the above meaning, by catalytic reduction with gaseous hydrogen in the presence of a catalyst, such as platinum oxide or Raney nickel, at ambient temperature or heating under atmospheric pressure or an elevated pressure, the starting materials being in the form of a solution in aqueous ammonia or ammonia and alcohol.

The corresponding compounds wherein $R^1$ is acetamido can be prepared either by acetylation of these amino compounds, as with acetic anhydride, a mixture of acetic acid and acetic anhydride or acetyl chloride at ambient temperature or under heating, or catalytic reduction of the corresponding nitro compound with gaseous hydrogen in the presence of a catalyst, such as palladium-carbon or platinum oxide, at ambient temperature or heating under atmospheric pressure or elevated pressure in the presence of acetic anhydride.

These acetamido compounds can be hydrolyzed with a mineral acid such as hydrochloric acid or sulfuric acid or with a caustic alkali, an alkaline earth metal or alkali metal carbonate in water, an alcohol or a mixture thereof, to yield the corresponding amino compounds.

These hydroxy compounds can be acetylated to yield the corresponding compounds where one or both of $R^1$ and $R^2$ are acetoxy.

The compounds wherein one or both of $R^1$ and $R^2$ are hydroxy can be obtained from the corresponding mono- or di-hydroxy compound by heating in the presence of an acid, preferably a hydrohalogenic acid, in a lower alcohol or in water as a solvent under atmospheric or elevated pressure.

The compounds wherein R is lower alkoxy can be obtained from the corresponding compound wherein R is hydroxy by esterification with a lower alkanol in the presence of an acid catalyst. These esters can be saponified to yield the corresponding acid, optionally after modification of for example $R^1$ and/or $R^2$. Alternatively, the esters can be amidated to yield the compounds of Formula I where R is

These amides can also be prepared directly from the acids and amines optionally through intermediate preparation of a reactive acylating derivative such as an acid halide.

The compounds of the present invention are hypotensive agents, presumably as a result of their ability to inhibit dopamine-$\beta$-hydroxylase.

The pharmacological action of the product of the present invention can be conventionally observed as follows: 50 mg/kg of a sample was administered orally to spontaneously hypertensive rats (male 20–40 weeks age) and percent decrease in blood pressure after 1, 2, 3 and 5 hours was determined, using the known fusaric acid as a reference. Acute toxicity of the compounds was determined by introperitoneal administration of the samples to ddY male mice (6 weeks age), followed by calculation of the values after observation for one week. The results are as follows:

| Compounds | $LD_{50}$ mg/Kg | % Decrease | | | |
|---|---|---|---|---|---|
| | | 1hr. | 2hrs. | 3hrs. | 5hrs. |
| Fusaric acid (reference) | 80 | 15.6 | 21.3 | 16.5 | 21.0 |
| 5-Benzylpicolinic acid | 138 | 12.7 | 19.0 | 24.9 | 29.5 |
| 5-(4-Methoxybenzyl)-picolinic acid | 132 | 24.8 | 28.1 | 23.4 | 21.9 |
| 5-(2-Methoxybenzyl)-picolinie acid | 177 | 25.9 | 26.9 | 26.0 | 25.5 |
| 5-(4-Chlorobenzyl)-picolinic acid | 120 | 26.4 | 42.1 | 48.6 | 50.3 |
| 5-(4-Nitrobenzyl)-picolinic acid | 177 | — | — | — | 39.8 |
| Methyl 5-benzylpicolinate | 88 | — | — | — | 48.8 |
| Ethyl 5-benzylpicolinate (Hydrochloride) | 140 | — | — | — | 32.4 |
| 5-Benzylpicolinic acid N- | | | | | |

| Compounds | LD$_{50}$ mg/Kg | % Decrease 1hr. | 2hrs. | 3hrs. | 5hrs. |
|---|---|---|---|---|---|
| benzylamide | 707 | — | — | — | 27.1 |

The dopamine-$\beta$-hydroxylase inhibitory activity can be seen from the following table, some of the compounds of this invention having more potent activities than that of the known fusaric acid. Acute toxicities (LD$_{50}$) were determined as above:

| Compounds | LD$_{50}$ (i.p.) mg/kg | ID$_{50}$ g/ml |
|---|---|---|
| Fusaric Acid (control) | 80 | $1.5 \times 10^{-8}$ |
| Picolinic Acid (control) | — | $1.0 \times 10^{-6}$ |
| 5-(4-Aminobenzyl)-picolinic Acid | — | $7.6 \times 10^{-8}$ |
| 5-(4-Hydroxybenzyl)-picolinic Acid | 193 | $8.9 \times 10^{-9}$ |
| Methyl 5-(4-hydroxybenzyl)-picolinate | 1000 | $7.0 \times 10^{-9}$ |
| Ethyl 5-(4-hydroxybenzyl)-picolinate | 594 | $7.1 \times 10^{-9}$ |
| 5-(2-Hydroxybenzyl)-picolinic Acid | 354 | $2.1 \times 10^{-8}$ |
| 5-(3,4-Dihydroxybenzyl)-picolinic Acid | 561 | $8.8 \times 10^{-9}$ |

The pharmaceutical compositions of the present invention contain a major or minor amount, e.g. 99.5% to 0.1%, preferably 95% to 0.5%, of a 5-benzylphenopicolinic acid or a salt thereof in combination with a pharmaceutically acceptable nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of phenopicolinic acid corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired antihypertensive effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgement and considering the age, weight and condition of the recipient, the route of administration and the nature and gravity of the hypertensive condition, generally the dosage will be from about 15 to about 100, preferably 20 to 45, mg/kg of body weight per day when given orally, and from about 3 to about 20, preferably from 7 to 15, mg/kg of body weight per day when given parenterally. In some instances a sufficient antihypertensive effect can be obtained at a lower dose while in others, a larger dose will be required.

Typical daily doses for hypertensive patient of about 70 kg body weight are thus from about 100 to 800 mg, preferably 150 to 30 mg, and typical parenteral doses are from 20 to 150 mg, preferably 50 to 100 mg.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or and absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The 5-benzylphenopicolinic acid and its salts can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined about of 5-benzylphenopicolinic acid. Syrups can be prepared by dissolving the compound or a salt thereof in a suitable flavored aqueous sucrose solution while elixirs are prepared through the use of a non-toxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of 5-benzylphenopicolinic acid is placed in a vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

The following examples will serve to further typify the nature of this invention without being a limitation on the scope thereof.

EXAMPLE 1

Preparation of 5-benzylpicolinic acid:

22.4 Grams of 5-benzyl-2-methylpyridine were dissolved in 100 ml. of pyridine. The resulting solution was then added with 40.7 g of selenium dioxide and the whole was heated under reflux for 5 hours. The reaction solution was subjected to filtration. The filtrate was concentrated under reduced pressure and then added with ether. Crystals thus precipitated were collected by filtration, dissolved in hot ethanol, treated with active carbon and allowed to cool to obtain 19.9 g of 5-benzyl-picolinic acid of a melting point of 145°~147° C.

EXAMPLE 2

Preparation of 5-(4-methoxybenzyl)picolinic acid:

5.3 Grams of 5-(4-methoxybenzyl)-2-methylpyridine were dissolved in 6 ml. of acetic acid. The resulting solution was added with 3.2 g of 30% hydrogen peroxide and the whole was heated at 80°~90° C. for 24 hours. The reaction solution was diluted with ice-water, neutralized with dilute aqueous ammonia and subjected to extraction with chloroform. After washing with water and drying, the solvent was distilled out to obtain the N-oxide substantially quantitatively. The N-oxide was added with 18 ml. of acetic anhydride and the whole was refluxed for one hour. Excessive acetic anhydride was distilled out and the residue was subjected to reduce pressure distillation. A fraction boiling at 200°~205° C. (5 mmHg) was collected. Thus, 4.4 g of 2-acetoxymethyl-5-(4-methoxybenzyl)pyridine were obtained as viscous oily product. From the acetate thus obtained, a part of 2.8 g was dissolved in 10 ml. of ethanol. The solution was then added with 3 ml. of 10% aqueous NaOH solution. After reflux for 1.5 hours, the reaction solution was diluted with water and subjected to extraction with ether. After distillation of the solvent, 2.1 g of 2-hydroxymethyl-5-(4-methoxybenzyl)pyridine were obtained as crystals at a melting point of 55°~58° C.

5.6 Grams of the hydroxymethyl compound were dissolved in 30 ml. of t.-butanol, added with 10 ml. of water and then with a solution of 4.48 g of potassium permanganate in 50 ml. of water slowly under cooling with ice and stirring. After stirring at an internal temperature of 1°~5° C. for additional one hour, the reaction solution was subjected to filtration. The filtrate was adjusted to pH 3 with 10% hydrochloric acid and then subjected to extraction with chloroform. After chloroform was distilled out, the residue was recrystallized from methanol to obtain 4.5 g of 5-(4-methoxybenzyl)-picolinic acid of a melting point of 145°~147° C.

In the same manner as in Example 1 or 2, the following compounds were synthesized:

|  | Melting point |
| --- | --- |
| 5-(4-Methylbenzyl)picolinic acid | 162 ~ 164° C. |
| 5-(4-Chlorobenzyl)picolinic acid | 148 ~ 152° C. |
| 5-(2-Chlorobenzyl)picolinic acid | 171 ~ 173° C. |
| 5-(4-Bromobenzyl)picolinic acid | 166 ~ 168° C. |

-continued

|  | Melting point |
| --- | --- |
| 5-(4-Ethoxybenzyl)picolinic acid | 142 ~ 144° C. |
| 5-(2-Methoxybenzyl)picolinic acid | 171 ~ 173° C. |
| 5-(3,4-Dimethoxybenzyl)picolinic acid | 131 ~ 133° C. |
| 5-(4-Nitrobenzyl)picolinic acid | 181 ~ 183° C. |

EXAMPLE 3

Preparation of 5-(4-nitrobenzyl)picolinic acid:

3.55 Grams of sodium nitrate were pulverized. The resulting powder was mixed with 7.0 g of 5-benzylpicolinic acid to obtain homogeneous mixture. The mixture was added slowly to 70 ml. of concentrated sulfuric acid, while reaction temperature was kept in the range of from −5° C to 0° C. After three hours, the mixture was poured into about 200 ml. of ice-water. Aqueous ammonia was added thereto to adjust it to pH 2–3. Precipitates thus formed were filtered out and then recrystallized from ethyl alcohol to obtain 5.4g of 5-(4-nitrobenzyl)picolinic acid of a melting point of 178°–182° C.

EXAMPLE 4

Preparation of methyl 5-(4-nitrobenzyl)picolinate:

6.0 Grams of methyl 5-benzylpicolinate were dissolved in 20 ml. of concentrated sulfuric acid at room temperature. A solution of 2.7 g of sodium nitrate in 20 ml. of concentrated sulfuric acid was added dropwise thereto under cooling to keep internal temperature at 5° C. After three hours, the reaction solution was poured into ice-water and neutralized with sodium carbonate. After extraction with ethyl acetate, washing with water and drying, the solvent was distilled out. The residue was recrystallized from methanol to obtain 3.5 g of 172°–178° C.

EXAMPLE 5

Preparation of methyl 5-(4-acetaminobenzyl)picolinate:

3.0 Grams of methyl 5-(4-nitrobenzyl)picolinate were dissolved in 150 ml. of a mixture of acetic acid and acetic anhydride (4:1). The resulting solution was added with 6.0 g of 5% palladium-carbon. Catalytic reduction was carried out at room temperature under atmospheric pressure. After 1.5 hours, the reaction solution was subjected to filtration and the filtrate was concentrated under reduced pressure. The residue was added with n-hexane to form crystals. The crystals were recrystallized from a solvent comprising a mixture of chloroform/n-hexane to obtain 1.5 g of methyl 5-(4-acetaminobenzyl)picolinate.

EXAMPLE 6

Preparation of methyl 5-(4-acetaminobenzyl)picolinate:

One gram of methyl 5-(4-aminobenzyl)picolinate were heated together with 10 ml. of acetic anhydride under reflux for two hours. The reaction mixture was concentrated under reduced pressure. The residue was added with n-hexane to form crystals. The crystals were then recrystallized from a solvent comprising a mixture of chloroform/n-hexane to obtain 0.8 g of methyl 5-(4-acetaminobenzyl)-picolinate of a melting point of 175°–177° C.

EXAMPLE 7

Preparation of 5-(4-aminobenzyl)picolinic acid dihydrochloride:

a. 0.8 Gram of methyl 5-(4-acetaminobenzyl)picolinate and 20 ml. of concentrated hydrochloric acid were heated under reflux for 3 hours. Then, concentrated hydrochloric acid was distilled out under reduced pressure. Ethyl alcohol was added thereto and thus resulting crystals were collected by filtration and dried at room temperature under reduced pressure to obtain 0.7 g of 5-(4-aminobenzyl)picolinic acid dihydrochloride as colorless crystals of a decomposition point of 217°–223° C.

b. 1.0 Gram of 5-(4-nitrobenzyl)picolinic acid was dissolved in 50 ml. of 10% aqueous ammonia solution. The resulting solution was added with 2.0 g of Raney nickel catalyst and then gaseous hydrogen was introduced therein under stirring under atmospheric pressure. After two hours, the reaction solution was subjected to filtration and the filtrate was concentrated to dryness under reduced pressure. The residue was added with 3 ml. of concentrated hydrochloric acid and concentrated again under reduced pressure. Ethanol was added thereto and the resulting crystals were collected by filtration to obtain 0.6 g of 5-(4-aminobenzyl)picolinic acid dihydrochloride.

EXAMPLE 8

Preparation of 5-(4-hydroxybenzyl)picolinic acid:

Five milliliters of 47% hydrobromic acid were added to 1.5 g of 5-(4-methoxybenzyl)picolinic acid. The mixture was heated under reflux for three hours. After allowing to cool, the reaction mixture was adjusted to around pH 2 with 10% aqueous NaOH solution to form crystals. The crystals were collected by filtration and then recrystallized from methanol to obtain 1.0 g of 5-(4-hydroxybenzyl)-picolinic acid as crystals of a melting point of 213°~215° C.

EXAMPLE 9

Preparation of 5-(3,4-dihydroxybenzyl)picolinic acid:

Twenty milliliters of 48% hydrobromic acid were added to 1.5 g of 5-(3,4-dimethoxybenzyl)picolinic acid. The mixture was heated under reflux for 6 hours. After allowing to cool, crystals formed were collected by filtration. The crystals were dissolved in 10% aqueous ammonia, treated with active carbon and adjusted to pH 2-3 with dilute hydrochloric acid to form crystals. The crystals were collected by filtration to obtain 0.8 g of 5-(3,4-dihydroxybenzyl)picolinic acid as reddish brown crystals of a decomposition point of 246°~249° C.

EXAMPLE 10

Preparation of ethyl 5-(4-hydroxybenzyl)picolinate:

One gram of ethyl 5-(4-methoxybenzyl)picolinate was dissolved in 20 ml. of ethyl alcohol saturated with hydrochloric acid. The solution was heated in a sealed tube at 120° C. for 24 hours. The solvent was distilled out and the residue was added with cold water. Crystals thus formed were collected by filtration and recrystallized from ethyl acetate to obtain 0.8 g of ethyl 5-(4-hydroxybenzyl)-picolinate as colorless needle-like crystals of a melting point of 153°~156° C.

EXAMPLE 11

Preparation of 5-(4-acetoxybenzyl)picolinic acid:

0.7 Gram of 5-(4-hydroxybenzyl)picolinic acid was dissolved in 6 ml. of pyridine. The resulting solution was then added with 2 ml. of acetic anhydride dropwise under ice-cooling and stirring. The whole was allowed to stand at room temperature for 18 hours. The reaction solution was acidified with hydrochloric acid and then subjected to extraction with ethyl acetate. After washing with water and drying, the solvent was distilled out and the residue was recrystallized from benzene to obtain 0.3 g of 5-(4-acetoxybenzyl)picolinic acid as colorless needle-like crystals of a melting point of 116°–119° C.

EXAMPLE 12

Preparation of 5-benzylpicolinic acid N-ethylamide:

2.1 Grams of 5-benzylpicolinic acid were dissolved in 20 ml. of chloroform. The resulting solution was then added with 1.2 g of triethylamine and 1.1 g of ethyl chlorocarbonate and thereafter with 33% ethylamine solution dropwise under ice-cooling and stirring. After 30 minutes 10 ml. of water were added thereto and the mixture was fractionated. The organic layer was washed with 10% aqueous ammonia. After drying, the solvent was distilled out. The residue was recrystallized from n-hexane to obtain 2.0 g of 5-benzyl-picolinic acid N-ethylamide as colorless crystals of a melting point of 77°~78° C.

EXAMPLE 13

Preparation of ethyl 5-benzylpicolinate hydrochloride:

2.0 Grams of 5-benzylpicolinic acid were suspended in 25 ml. of ethanol. The resulting suspension was saturated with hydrogen chloride gas under ice-cooling. After reflux for three hours, the reaction solution was concentrated under reduced pressure. Ether was added thereto to form crystals. The crystals were then recrystallized from a solvent comprising a mixture of acetone/ether to obtain 1.7 g of ethyl 5-benzylpicolinate of a melting point of 109°~111° C.

EXAMPLE 14

Preparation of methyl 5-(4-hydroxybenzyl)-picolinate:

One gram of 5-(4-hydroxybenzyl)-picolinic acid was suspended in 15 ml. of methanol. Then, hydrogen chloride gas was introduced therein till saturation. After heating under reflux for 5 hours, the reaction mixture was concentrated under reduced pressure. The residue was added with cold water to form crystals. The crystals were then recrystallized from ethyl acetate to obtain 0.85 g of methyl 5-(4-hydroxybenzyl)picolinate as colorless needlelike crystals of a melting point of 184°~186° C.

EXAMPLE 15

Preparation of 5-benzylpicolinic acid amide:

To one gram of ethyl 5-benzylpicolinate, 10 ml. of 28% aqueous ammonia were added. After allowing the mixture to stand at room temperature for 24 hours, crystals formed were collected by filtration and recrystallized from ethanol to obtain 0.6 g of 5-benzylpicolinic acid amide as colorless crystals of a melting point of 193°~196° C.

In the same manner as above, the following compounds were synthesized.

|  | Melting point |
| --- | --- |
| 5-Benzylpicolinic acid N,N-diethylamide hydrochloride | 120 ~ 123° C. |
| 5-Benzylpicolinic acid N-benzylamide | 74 ~ 75° C. |
| 5-Benzylpicolinic acid anilide | 116 ~ 118° C. |
| Methyl 5-benzylpicolinate | 67 ~ 68° C. |
| 5-(2-Methoxybenzyl)picolinic acid amide | 157 ~ 160° C. |
| Ethyl 5-(4-hydroxybenzyl)picolinate | 153 ~ 156° C. |
| Methyl 5-(4-methoxybenzyl)picolinate | 49 ~ 51° C. |
| Methyl 5-(4-acetaminobenzyl)picolinate | 175 ~ 177° C. |
| Methyl 5-(4-nitrobenzyl)picolinate | 175 ~ 178° C. |

What is claimed is:

1. A compound of the formula:

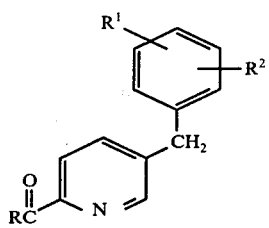

wherein

R is hydroxy, lower alkoxy or

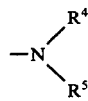

in which each of $R^4$ and $R^5$, independently of the other, is hydrogen, lower alkyl, benzyl, phenethyl or phenyl; and each of $R^1$ and $R^2$, independently of the other, is hydrogen, lower alkyl, halo, lower alkoxy, nitro, amino, acetamido, hydroxy or acetoxy, and the pharmaceutically acceptable salts thereof.

2. A compound according to claim 1 wherein R is hydroxy.

3. A compound according to claim 1 wherein R is lower alkoxy.

4. A compound according to claim 1 wherein R is

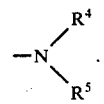

5. A compound according to claim 1 wherein one of $R^1$ and $R^2$ is other than hydrogen.

6. A compound according to claim 5 wherein $R^1$ and $R^2$ are each hydroxy or methoxy.

7. A compound according to claim 5 wherein $R^2$ is hydrogen and $R^1$ is other than hydrogen.

8. A compound according to claim 7 wherein $R^1$ is methyl, chloro, bromo, methoxy, ethoxy, nitro, amino, acetamido or acetoxy.

9. A compound according to claim 8 wherein $R^1$ is in the 2- or 4-position of the depicted benzyl group.

10. A compound according to claim 7 wherein $R^1$ is hydroxy.

11. The compound according to claim 1 which is 5-benzylpicolinic acid.

12. The compound according to claim 1 which is 5-(4-methoxybenzyl)-picolinic acid.

13. The compound according to claim 1 which is 5-(2-methoxybenzyl)-picolinic acid.

14. The compound according to claim 1 which is 5-(4-chlorobenzyl)-picolinic acid.

15. The compound according to claim 1 which is 5-(4-nitrobenzyl)-picolinic acid.

16. The compound according to claim 1 which is methyl-5-benzylpicolinate.

17. The compound according to claim 1 which is ethyl-5-benzylpicolinate.

18. The compound according to claim 1 which is 5-benzylpicolinic acid N-benzylamide.

19. The compound according to claim 1 which is 5-(4-aminobenzyl)-picolinic acid.

20. The compound according to claim 1 which is 5-(4-hydroxybenzyl)-picolinic acid.

21. The compound according to claim 1 which is methyl-5-(4-hydroxybenzyl)-picolinate.

22. The compound according to claim 1 which is ethyl-5-(4-hydroxybenzyl)-picolinate.

23. The compound according to claim 1 which is 5-(2-hydroxybenzyl)-picolinic acid.

24. The compound according to claim 1 which is 5-(3,4-dihydroxybenzyl)-picolinic acid.

25. The method of effecting a hypotensive response in humans and other animals which comprises administering thereto a compound according to claim 1.

26. A hypotensive pharmaceutical composition comprising an effective amount of a compound according to claim 1 and a pharmaceutically acceptable nontoxic carrier.

* * * * *